United States Patent
Deslauriers (10) Patent No.: US 11,534,601 B2
(45) Date of Patent: Dec. 27, 2022

(54) PERFORATED HYDROGEL CONFIGURATIONS AND METHODS OF PRODUCTION AND USE THEREOF

(71) Applicants: Novocure GmbH, Root (CH); Novocure GmbH, Root (CH)

(72) Inventor: Richard Deslauriers, Woodbury, CT (US)

(73) Assignee: Novocure GmbH, Root (CH)

( * ) Notice: Subject to any disclaimer, the term of this patent is extended or adjusted under 35 U.S.C. 154(b) by 76 days.

(21) Appl. No.: 17/091,186

(22) Filed: Nov. 6, 2020

(65) Prior Publication Data

US 2021/0138233 A1    May 13, 2021

Related U.S. Application Data

(60) Provisional application No. 62/956,916, filed on Jan. 3, 2020, provisional application No. 62/955,563, filed on Dec. 31, 2019, provisional application No. 62/932,653, filed on Nov. 8, 2019.

(51) Int. Cl.
*A61N 1/04* (2006.01)
*A61N 1/36* (2006.01)
*C08J 3/075* (2006.01)

(52) U.S. Cl.
CPC .......... *A61N 1/0496* (2013.01); *A61N 1/044* (2013.01); *A61N 1/0476* (2013.01); *A61N 1/36002* (2017.08); *C08J 3/075* (2013.01); *C08J 2301/02* (2013.01); *C08J 2333/02* (2013.01); *C08J 2339/06* (2013.01)

(58) Field of Classification Search
CPC .... A61N 1/0496; A61N 1/044; A61N 1/0476; A61N 1/0492; A61N 1/0529; A61N 1/36002
See application file for complete search history.

(56) References Cited

U.S. PATENT DOCUMENTS

| | | | |
|---|---|---|---|
| 5,622,168 A * | 4/1997 | Keusch | A61B 5/282 607/152 |
| 5,938,597 A | 8/1999 | Stratbucker | |
| 5,974,344 A * | 10/1999 | Shoemaker, II | A61N 1/0468 607/152 |
| 7,565,205 B2 * | 7/2009 | Palti | A61N 1/40 607/76 |
| 8,715,203 B2 | 5/2014 | Palti | |
| 2003/0069627 A1 * | 4/2003 | Giuntoli | A61H 39/002 607/149 |
| 2004/0122500 A1 | 6/2004 | Rouns | |
| 2018/0295708 A1 * | 10/2018 | Trutwig | A61L 2/0011 |

FOREIGN PATENT DOCUMENTS

WO    WO03002185 A2    1/2003

OTHER PUBLICATIONS

Notification of Transmittal of the International Search Report and Written Opinion of the International Searching Authority dated Feb. 12, 2021, Application No. PCT/US2020/059437, 13 pages.

* cited by examiner

*Primary Examiner* — Mallika D Fairchild
(74) *Attorney, Agent, or Firm* — Dunlap Codding, P.C.

(57) ABSTRACT

Improved hydrogel configurations for use with a TTField-generating system is disclosed. Also disclosed are kits containing the improved hydrogel configurations and methods of producing and using the improved hydrogel configurations.

21 Claims, 5 Drawing Sheets

PERFORATED HYDROGEL CONFIGURATIONS AND METHODS OF PRODUCTION AND USE THEREOF

CROSS REFERENCE TO RELATED APPLICATIONS/INCORPORATION BY REFERENCE STATEMENT

The present patent application claims priority to Provisional Patent Application U.S. Ser. No. 62/932,653 entitled "CONDUCTIVE GEL COMPOSITIONS AND METHODS OF PRODUCTION AND USE THEREOF", filed Nov. 8, 2019; Provisional Patent Application U.S. Ser. No. 62/955,563 entitled "PERFORATED HYDROGEL CONFIGURATIONS AND METHODS OF PRODUCTION AND USE THEREOF", filed Dec. 31, 2019; and Provisional Patent Application U.S. Ser. No. 62/956,916 entitled "PERFORATED HYDROGEL CONFIGURATIONS AND METHODS OF PRODUCTION AND USE THEREOF", filed Jan. 3, 2020, the entire contents of which are hereby expressly incorporated herein by reference.

STATEMENT REGARDING FEDERALLY SPONSORED RESEARCH OR DEVELOPMENT

Not Applicable.

BACKGROUND

Tumor Treating Fields (TTFields or TTFs) are low intensity (e.g., 1-3 V/cm) alternating electric fields within the intermediate frequency range (100-500 kHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776. TTFields are typically delivered through two pairs of transducer arrays that generate perpendicular fields within the treated tumor; the electrode arrays that make up each of these pairs are positioned on opposite sides of the body part that is being treated. More specifically, for the OPTUNE® system (Novocure Limited, St. Helier, Jersey), one pair of electrodes is located to the left and right (LR) of the tumor, and the other pair of electrodes is located anterior and posterior (AP) to the tumor. TTFields are approved for the treatment of glioblastoma multiforme (GBM), and may be delivered, for example, via the OPTUNE® system, which includes transducer arrays placed on the patient's shaved head.

Each transducer array used for the delivery of TTFields in the OPTUNE® device comprises a set of ceramic disk electrodes, which are coupled to the patient's skin (such as, but not limited to, the patient's shaved head for treatment of GBM) through a layer of conductive medical gel. The purpose of the medical gel is to deform to match the body's contours and to provide good electrical contact between the arrays and the skin; as such, the gel interface bridges the skin and reduces interference. The device is intended to be continuously worn by the patient for 2-4 days before removal for hygienic care and re-shaving (if necessary), followed by reapplication with a new set of arrays. As such, the medical gel remains in substantially continuous contact with an area of the patient's skin for a period of 2-4 days at a time, and there is only a brief period of time in which the area of skin is uncovered and exposed to the environment before more medical gel is applied thereto.

Various types of medical gels are known in the art. One particular type of gel useful as part of a TTField-generating system is a conductive hydrogel. Hydrogels are three-dimensional (3-D) networks of hydrophilic polymers that can swell in water and hold a large amount of water while maintaining their structure due to chemical or physical cross-linking of individual polymer chains. Hydrogels are used in many fields, which include the medical sciences if the hydrogels are nontoxic and compatible with biological environments. (Bahram et al. (2016) "An Introduction to Hydrogels and Some Recent Applications." *Emerging Concepts in Analysis and Applications of Hydrogels*. InTech Open).

However, dermatologic adverse events (dAEs) have been observed with the use of existing medical grade hydrogels with TTField generating systems at an incidence rate of 16% and 22% in the phase III trial and the post-marketing surveillance program, respectively; these dAEs include (but are not limited to) allergic and irritant dermatitis, macerations, mechanical lesions, ulcers, and skin infections. In particular, irritant contact dermatitis and allergic contact dermatitis can arise from chemical irritation from and allergy to the hydrogel, respectively, while maceration of the skin due to prolonged exposure to the hydrogel can cause lesions/ulcers on the skin, and these lesions/ulcers are subsequently susceptible to infection. These adverse events are exacerbated by the requirement that the hydrogel remain in continuous contact with the patient's skin for multiple days at a time without an extended period of "breathability" between application of TTField arrays to the skin. (Lacouture et al. (2014) *Seminars in Oncology*, 41:S1-S14).

Currently available medical hydrogels typically have pH's that are too acidic for long term wear and thus are damaging to the skin upon extended exposure thereto. In addition, the bottom liner adhesion (i.e., skin adhesion) rate for the currently available hydrogels typically is not high enough to provide the necessary level of attachment to skin for the wear time required. Also, adjustment of either of these two properties can increase the resistivity of the hydrogel, thus affecting the ability of the hydrogel to pass electrical current therethrough. In addition, when a hydrogel comes into contact with sweat over the wear period, the hydrogel swells and degrades, which increases resistivity. Further, loss of the hydrogel interface over the approximately three-day wear period (such as, but not limited to, by erosion of the adhesiveness and conductivity of the hydrogel) reduces the standard current/electric field generated by the TTField system and thus decreases the functionality and overall effectiveness of the TTField treatment.

For a further discussion on the general properties of hydrogels, please refer to Okay, Oguz. (1970). General Properties of Hydrogels. 10.1007/978-3-540-75645-3_1.

Because of this extended exposure and the concomitant unique usage of hydrogels with the TTField system, new and improved conductive hydrogel configurations are desired that possess multiple properties that are unique and vary from the properties typically possessed by currently available medical grade hydrogels. It is to such conductive hydrogel configurations, as well as kits containing same and methods of producing and using same, that the present disclosure is directed.

DETAILED DESCRIPTION

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, and published patent applications referenced in any portion of this application are herein expressly incorporated by reference in their entirety to the same extent as if each individual patent or publication was specifically and individually indicated to be incorporated by reference.

All of the compositions, kits, and/or methods disclosed herein can be made and executed without undue experimentation in light of the present disclosure. While the compositions, kits, and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "polypeptide" as used herein will be understood to refer to a polymer of amino acids. The polymer may include d-, l-, or artificial variants of amino acids. In addition, the term "polypeptide" will be understood to include peptides, proteins, and glycoproteins.

The term "polynucleotide" as used herein will be understood to refer to a polymer of two or more nucleotides. Nucleotides, as used herein, will be understood to include deoxyribose nucleotides and/or ribose nucleotides, as well as artificial variants thereof. The term polynucleotide also includes single-stranded and double-stranded molecules.

The terms "analog" or "variant" as used herein will be understood to refer to a variation of the normal or standard form or the wild-type form of molecules. For polypeptides or polynucleotides, an analog may be a variant (polymorphism), a mutant, and/or a naturally or artificially chemically modified version of the wild-type polynucleotide (including combinations of the above). Such analogs may have higher, full, intermediate, or lower activity than the normal form of the molecule, or no activity at all. Alternatively and/or in addition thereto, for a chemical, an analog may be any structure that has the desired functionalities (including alterations or substitutions in the core moiety), even if comprised of different atoms or isomeric arrangements.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "pharmaceutically acceptable" refers to compounds and compositions which are suitable for administration to humans and/or animals without undue adverse side effects such as (but not limited to) toxicity, irritation, and/or allergic response commensurate with a reasonable benefit/risk ratio.

The term "pharmaceutically-acceptable excipient" refers to any carrier, vehicle, and/or diluent known in the art or otherwise contemplated herein that may improve solubility, deliverability, dispersion, stability, and/or conformational integrity of the compositions disclosed herein.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue.

The term "treatment" refers to both therapeutic treatment and prophylactic or preventative measures. Those in need of treatment include, but are not limited to, individuals already having a particular condition/disease/infection as well as individuals who are at risk of acquiring a particular condition/disease/infection (e.g., those needing prophylactic/preventative measures). The term "treating" refers to administering an agent/element/method to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

The terms "administration" and "administering," as used herein, will be understood to include all routes of administration known in the art, including but not limited to, oral, topical, transdermal, parenteral, subcutaneous, intranasal, mucosal, intramuscular, intraperitoneal, intravitreal, and intravenous routes, and including both local and systemic applications. In addition, the compositions of the present disclosure (and/or the methods of administration of same) may be designed to provide delayed, controlled, or sustained release using formulation techniques which are well known in the art.

Turning now to the inventive concept(s), certain non-limiting embodiments thereof are directed to conductive gel compositions comprising a perforated configuration for application to a patient's skin during treatment with a TTField-generating system.

The presently disclosed and/or claimed inventive concept(s), including, without limitation, conductive gels having perforated configurations, may be utilized with any existing conductive gels commonly known in the art so long as the conductive gels have sufficient structural integrity to maintain the perforations or protrusions for a period of time sufficient to treat a patient before removal and/or replacement of the conductive gel. In one non-limiting embodiment, the conductive gel composition having a perforated configuration(s) has at least one of a decreased polymer chain length and an added free salt when compared to existing gel compositions; the decrease in polymer chain length and increase in free salt concentration maximizes the conductivity of the gel while reducing the occurrence of skin irritation caused by the conductive gel. The perforations (or protrusions) on a surface of the improved conductive gel allow for increased air flow between a patient's skin and the conductive gel thereby reducing, if not eliminating, macerations, lesions/ulcers, and dermatitis, as well as allowing for a decrease in operating temperature when a TTField is applied to the perforated gel. In addition, by decreasing the area of the conductive gel by increasing the number of perforations, adhesion of the gel to a substrate is increased.

Certain non-limiting embodiments of the present disclosure are directed to a composition that includes a semi-solid, perforated conductive gel for application to a patient's skin and for placement between the patient's skin and at least one transducer array that generates an alternating electric field having a frequency in a range of from about 50 kHz to about 500 kHz. While the presently disclosed and/or claimed inventive concept(s) are applicable to any conductive gel(s) commonly known in the art, in certain particular (but non-limiting) embodiments, the perforated, conductive gel comprises a free salt present via incorporation within the gel or as one layer of a multi-layered gel (i.e., a bilayered gel). The term "free salt" refers to salt molecules that are not incorporated as part of the polymerized chain structure but rather are floating substantially freely within the gel and thus are a source of free ions that conduct electricity and thus reduce impedance.

Alternatively and/or in addition thereto, in a particular non-limiting embodiment, the perforated, conductive gel comprises one or more of the following chemical and structural features/properties: a polymer chain length in a range of from about 1 nm to about 200 nm; a free salt present at a concentration in a range of from about 0.1 mM to about 1 M; a pH in a range of from about 6 to about 8; a volume resistivity of less than about 100 Ohm-in; and a skin adhesion rate of at least about 100 g/inch.

In addition, given the prolonged exposure of the conductive gel composition to the patient's skin, the gel should be optimized for use at body temperature (i.e., in a range of from about 34° C. to about 40° C.). At these temperatures, the air flow introduced by the perforations to the improved perforated, conductive gel maximizes evaporative cooling thereby allowing for a reduced operating temperature and cooling effect to the patient's skin.

In certain particular (but non-limiting) embodiments, the alternating electric field is generated within a target region of the patient. The target region typically comprises at least one tumor, and the generation of the alternating electric field selectively destroys or inhibits growth of the tumor. The alternating electric field may be generated at any frequency that selectively destroys or inhibits growth of the tumor. For example (but not by way of limitation), the alternating electric field may have a frequency of about 50 kHz, about 75 kHz, about 100 kHz, about 125 kHz, about 150 kHz, about 175 kHz, about 200 kHz, about 225 kHz, about 250 kHz, about 275 kHz, about 300 kHz, about 325 kHz, about 350 kHz, about 375 kHz, about 400 kHz, about 425 kHz, about 450 kHz, about 475 kHz, or about 500 kHz, as well as a range formed from any of the above values (i.e., a range of from about 100 kHz to about 300 kHz, a range of from about 100 kHz to about 150 kHz, a range of from about 150 kHz to about 300 kHz, etc.), and a range that combines two integers that fall between two of the above-referenced values (i.e., a range of from about 32 kHz to about 333 kHz, a range of from about 78 kHz to about 298 kHz, etc.). While described herein as primarily comprising an alternating electric field(s) or current, a person having ordinary skill in the art should readily appreciate that the presently disclosed and/or claimed inventive concept(s) further contemplate the use of direct electric field(s) or current.

In certain particular (but non-limiting) embodiments, the alternating electric field may be imposed at two or more different frequencies. When two or more frequencies are present, each frequency is selected from any of the above-referenced values, or a range formed from any of the above-referenced values, or a range that combines two integers that fall between two of the above-referenced values.

As previously mentioned, the conductive gel utilized in accordance with the presently disclosed and/or claimed inventive concept(s) may comprise any composition commonly known in the art and may be in any form that allows the gel to function in accordance with the present disclosure. For example (but not by way of limitation), the conductive gel may be in the form of a hydrogel or a hydrocolloid. In certain non-limiting embodiments, the conductive gel is a perforated, conductive polymerized hydrogel. In certain non-limiting embodiments, the conductive gel is perforated silicone.

In certain particular (but non-limiting) embodiments, the gel is sterile. In addition, in certain non-limiting embodiments, the gel will not substantially degrade upon exposure to sterilization conditions that include gamma rays or ethylene oxide gas.

The gel may be formed of any hydrophilic polymer that allows the gel to function in accordance with the present disclosure. For example (but not by way of limitation), the gel may be a polyacrylic acid gel, a povidone gel, or a cellulose gel. In addition, the gel may comprise at least one of chitosan, alginate, agarose, methylcellulose, hyaluronan, collagen, laminin, matrigel, fibronectin, vitronectin, poly-1-lysine, proteoglycans, fibrin glue, gels made by decellularization of engineered and/or natural tissues, as well as any combinations thereof. Further, the gel may comprise at least one of polyglycolic acid (PGA), polylactic acid (PLA), poly-caprolactone (PCL), polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), polyurethanes, poly(isopropylacrylamide), poly(N-isopropylacrylamide), or any combination thereof.

The polymers of the gel may be provided with any polymer chain length that allows the gel compositions to function as described herein. For example (but not by way of limitation), the polymer chain length may be about 1 nm, about 2 nm, about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, and above, as well as a range that combines any two of the above-referenced values (i.e., a range of from about 3 nm to about 175 nm, a range of from about 5 nm to about 150 nm, or a range of from about 10 nm to about 125 nm, a range of from about 15 nm to about 100 nm, etc.), and a range that combines two integers that fall between two of the above-referenced values (i.e., a range of from about 3 nm to about 157 nm, etc.).

In other non-limiting embodiments, the range of the polymer chain length is dependent upon the frequency(ies) of the alternating electric field. For example (but not by way of limitation), the range of the polymer chain length may be based upon a range of frequencies of the alternating electric field. Non-limiting examples include a range of from about 5 nm to about 50 nm when the alternating electric field has a frequency in a range of from about 50 kHz to about 150 kHz, a range of from about 50 nm to about 100 nm when the alternating electric field has a frequency in a range of from about 150 kHz to about 300 kHz, etc.

When present, the free salt present in the conductive gel may be any salt or other substance that serves as a source of free ions that are capable of floating substantially freely within the conductive gel (i.e., enhances ionic flow within the conductive gel), wherein the free ions serve to conduct electricity and thus reduce impedance. In certain particular (but non-limiting) embodiments, the free salt present in the conductive gel is a source of calcium ions, chloride ions, citrate ions, silver ions, iodide ions, etc., or any other ions that are known to be good conductors. Non-limiting examples of free salts that may be utilized in accordance with the present disclosure are salts that contain potassium (K), ammonium ($NH_4^+$), sodium (Na), calcium ($Ca^{2+}$), silver ($Ag^+$), nitrate, bicarbonate, and the like. Particular non-limiting examples of free salts that may be utilized in accordance with the present disclosure are NaCl, KCl, $CaCl_2$, $MgCl_2$, $ZnCl_2$, iodine, silver iodide (AgI), silver chloride (AgCl), silver dihydrogen citrate (SDC), sodium dihydrogen citrate, calcium bicarbonate, combinations thereof, and the like.

When present, the free salt present in the conductive gel may be provided with any concentration that allows the gel compositions to function as described herein. For example (but not by way of limitation), the free salt concentration may be at least about 0.1 mM, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, about 1 M, or higher, as well as any range that combines any two of the above-referenced values (i.e., a range of from about 0.1 mM to about 100 mM, a range of from about 1 mM to about 50 mM, etc.), and a range that combines two integers that fall between two of the above-referenced values (i.e., a range of from about 12 mM to about 550 mM, etc.).

In other non-limiting embodiments, the free salt concentration, when present, is dependent upon the frequency(ies) of the alternating electric field. For example (but not by way of limitation), the range of the free salt concentration may be based upon a range of frequencies of the alternating electric field. Non-limiting examples include a range of from about 0.1 mM to about 50 mM when the alternating electric field has a frequency in a range of from about 50 kHz to about 150 kHz, a range of from about 50 mM to about 100 mM when the alternating electric field has a frequency in a range of from about 150 kHz to about 300 kHz, etc.

While the non-limiting embodiments described herein above disclose that, when free salts are present, the free salts are dispersed in the conductive gel, it will also be understood that, free salts can also be present in layer(s) other than (or in addition to) the conductive gel. For example (but not by way of limitation), a separate layer may be located between the patient's skin and the conductive gel, and the free salts may be dispersed in this separate layer. In particular (but not by way of limitation), silver chloride divides into silver and chloride ions while on the skin, thereby assisting with the transfer of ions into the skin and enhancing the recovery rate as well as sensing ability.

The conductive gel may be provided with any pH that does not damage the skin of a patient or cause chemical irritation of the skin upon prolonged exposure to the gel. For example (but not by way of limitation), the gel may have a pH of about 6, about 6.5, about 7, about 7.5, about 8, as well as a range formed from any of the above values (i.e., a range of from about 6 to about 8, a range of from about 6.5 to about 7.5, etc.).

The conductive gel may be provided with any water content that allows the gel compositions to function as described herein and reduces any irritation of the skin upon prolonged exposure to the gel. For example (but not by way of limitation), the conductive gel may have a water concentration of less than or equal to about 70%, less than or equal to about 69%, less than or equal to about 68%, less than or equal to about 67%, less than or equal to about 66%, less than or equal to about 65%, less than or equal to about 64%, less than or equal to about 63%, less than or equal to about 62%, less than or equal to about 62%, less than or equal to about 60%, less than or equal to about 59%, less than or equal to about 58%, less than or equal to about 57%, less than or equal to about 56%, less than or equal to about 55%, less than or equal to about 54%, less than or equal to about 53%, less than or equal to about 52%, less than or equal to about 51%, less than or equal to about 50%, or lower, as well as any range that combines any two of the above-referenced values (i.e., a range of from about 50% to about 70%, a range of from about 50% to about 60%, a range of from about 52% to 58%, etc.).

In a particular (but non-limiting) embodiment, the conductive gel has a pH in a range of from about 6 to about 8, and a water concentration in a range of from about 50% to about 70%.

The conductive gel may be provided with any level of volume resistivity that maximizes the conductiveness of the conductive gel. For example (but not by way of limitation), the conductive gel may have a volume resistivity of less than about 100 Ohm-in, less than about 95 Ohm-in, less than about 90 Ohm-in, less than about 85 Ohm-in, less than about 80 Ohm-in, less than about 75 Ohm-in, less than about 70 Ohm-in, less than about 65 Ohm-in, less than about 60 Ohm-in, less than about 55 Ohm-in, less than about 50 Ohm-in, less than about 45 Ohm-in, less than about 40 Ohm-in, less than about 35 Ohm-in, less than about 30 Ohm-in, less than about 25 Ohm-in, less than about 20 Ohm-in, less than about 15 Ohm-in, less than about 10 Ohm-in, or lower, as well as a range formed of any of the above values (i.e., a range of from about 10 Ohm-in to about 100 Ohm-in, etc.) and a range that combines two integers that fall between two of the above-referenced values (i.e., a range of from about 13 Ohm-in to about 96 Ohm-in, etc.).

The conductive gel may be provided with any skin adhesion rate that allows the conductive gel to function in accordance with the present disclosure. For example (but not by way of limitation), the skin adhesion rate of the conductive gel may be at least about 50 g/inch width, at least about 60 g/inch, at least about 70 g/inch, at least about 80 g/inch, at least about 90 g/inch, about least about 100 g/inch, at least about 110 g/inch, at least about 120 g/inch, at least about 130 g/inch, at least about 140 g/inch, at least about 150 g/inch, at least about 160 g/inch, at least about 170 g/inch, at least about 180 g/inch, at least about 190 g/inch, at least about 200 g/inch, at least about 210 g/inch, at least about 220 g/inch, at least about 230 g/inch, at least about 240 g/inch, at least about 250 g/inch, at least about 260 g/inch, at least about 270 g/inch, at least about 280 g/inch, at least about 290 g/inch, at least about 300 g/inch, at least about 325 g/inch, at least about 350 g/inch, at least about 375 g/inch, at least about 400 g/inch, at least about 425 g/inch, at least about 450 g/inch, at least about 475 g/inch, at least about 500 g/inch, or higher, as well as a range of any of the above values (a range of from about 80 g/inch to about 90 g/inch, a range of from about 50 g/inch to about 140 g/inch, a range of from about 120 g/inch to about 300 g/inch, a range of from about 130 g/inch to about 500 g/inch, etc.), and a range that combines two integers that fall between two of the above-referenced values (i.e., a range of from about 115 g/inch to about 295 g/inch, etc.).

The conductive gel may be provided with any thickness that allows the conductive gel to function in accordance with the present disclosure. Non-limiting examples of thicknesses that may be utilized in accordance with the present disclosure include about 1 mil, about 5 mil, about 10 mil, about 15 mil, about 20 mil, about 25 mil, about 30 mil, about 35 mil, about 40 mil, about 45 mil, about 50 mil, about 55 mil, about 60 mil, about 65 mil, about 70 mil, about 75 mil, about 80 mil, about 85 mil, about 90 mil, about 95 mil, about 100 mil, or higher, as well as a range that combines any two of the above-referenced values (i.e., a range of from about 10 mil to about 50 mil, etc.), and a range that combines two integers that fall between two of the above-referenced values (i.e., a range of from about 12 mil to about 48 mil, etc.). However, a person having ordinary skill in the art should readily appreciate that the conductive gel (for instance, a hydrogel) may be any thickness capable of accomplishing the presently disclosed and/or claimed inventive concept(s) such that the conductive gel does not substantially dry out during treatment.

In certain particular (but non-limiting) embodiments, the conductive gel has a shelf life of at least about six months. For example (but not by way of limitation), the conductive gel has a shelf life of at least about 12 months.

In certain particular (but non-limiting) embodiments, (see FIG. 7) the conductive gel is a multi-layer structure that comprises: a scrim having a first and a second side with a gel tie layer attached to the first side of the scrim, and a gel skin layer attached to the second side of the scrim. The gel tie layer is designed for contact with the transducer array, while the gel skin layer is designed for contact with the patient's skin. The gel tie and gel skin layers are both formed of any of the conductive gels described or otherwise contemplated herein, and may be formed of the same or different conductive gels. The scrim may be formed of any material that allows the composition to function in accordance with the present disclosure; in particular, the material from which the scrim is formed is typically selected to optimize conductivity and minimize resistance of the composition. A non-limiting example of a material from which the scrim can be formed is spun nylon. In certain non-limiting embodiments, the conductive gel comprises and/or consists of at least one perforation extending through the entirety of the multi-layer structure. In certain non-limiting embodiments, the conductive gel comprises at least one male protrusion(s) extending from a side of the gel skin layer that engaged a patient's skin.

In addition, the composition may further include a removable top liner attached to the gel tie layer for protecting the gel tie layer until use, and/or a removable bottom liner attached to the gel skin layer for protecting the gel skin layer until use. Also, when the free salt is present as a separate layer, the composition may further include the free salt layer in between the gel skin layer and the removable bottom liner.

In certain particular (but non-limiting) embodiments, the conductive gel may further include at least one additive. Any type of additive that allows the conductive gel to function in accordance with the present disclosure and that may further enhance the conductivity and non-sensitizing properties of the conductive gel may be utilized in accordance with the present disclosure. Non-limiting examples of additives that may be utilized include at least one of an antibacterial agent, a vitamin, a moisturizer, or any combinations thereof, and the like.

Certain non-limiting embodiments of the present disclosure are directed to a kit that includes any of the gel-containing compositions disclosed or otherwise contemplated herein.

In certain particular (but non-limiting) embodiments, the kit may further include at least one pair of transducer arrays that generates an alternating electric field having a frequency in a range of from about 50 kHz to about 500 kHz upon application to a patient's skin in combination with the perforated gel composition (i.e., transducer arrays that function as part of a TTField-generating system). For example (but not by way of limitation), the kit may include at least about two pairs of transducer arrays, at least about four pairs of transducer arrays, at least about six pairs of transducer arrays, at least about eight pairs of transducer arrays, at least about ten pairs of transducer arrays, at least about 12 pairs of transducer arrays, at least about 14 pairs of transducer arrays, at least about 16 pairs of transducer arrays, at least about 18 pairs of transducer arrays, at least about 20 pairs of transducer arrays, at least about 22 pairs of transducer arrays, at least about 24 pairs of transducer arrays, at least about 26 pairs of transducer arrays, at least about 28 pairs of transducer arrays, at least about 30 pairs of transducer arrays, at least about 32 pairs of transducer arrays, at least about 34 pairs of transducer arrays, at least about 36 pairs of transducer arrays, at least about 38 pairs of transducer arrays, at least about 40 pairs of transducer arrays, at least about 42 pairs of transducer arrays, at least about 44 pairs of transducer arrays, at least about 46 pairs of transducer arrays, at least about 48 pairs of transducer arrays, at least about 50 pairs of transducer arrays, or more, as well as a range of pairs of transducer arrays that combines any two of the above-referenced values (i.e., a range of from about two pairs of transducer arrays to about 50 pairs of transducer arrays, a range of from about two pairs of transducer arrays to about 20 pairs of transducer arrays, etc.), and a range that combines two integers that fall between two of the above-referenced values (i.e., a range of from about one pair of transducer arrays to about 15 pairs of transducer arrays, etc.).

Examples of transducer arrays that function as part of a TTField system are known in the art and are described, for example but not by way of limitation, in U.S. Pat. Nos. 7,016,725; 7,089,054; 7,333,852; 7,565,205; 7,715,921; 8,170,684; 8,244,345; 8,715,203; 8,764,675; 10,188,851; and 10,441,776; and in US Patent Application Nos. US 2018/0160933; US 2019/0117956; US 2019/0307781; and US 2019/0308016. Therefore, no further description thereof is deemed necessary.

The perforated gel composition may be present in the kit in any form that allows the kit to perform in accordance with the present disclosure. For example, but not by way of limitation, the perforated conductive gel composition may be provided in the form of one or more sheets or one or more rolls. In addition, the perforated conductive gel composition may be provided in a single, individual unit/amount, or multiple units/amounts of the composition may be provided within the kit.

In addition to the components described in detail herein above, the kits may further contain other component(s)/reagent(s) for performing any of the particular methods described or otherwise contemplated herein. For example (but not by way of limitation), the kits may additionally include: (i) components for preparing the skin prior to disposal of the perforated gel composition and transducer arrays thereon (i.e., a razor, a cleansing composition or wipe/towel, etc.); (ii) components for removal of the gel/transducer array(s); and/or (iii) components for cleansing of the skin after removal of the gel/transducer array(s). The nature of these additional component(s)/reagent(s) will depend upon the particular treatment format and/or area/organ to be treated, and identification thereof is well within the skill of one of ordinary skill in the art; therefore, no further description thereof is deemed necessary. Also, the components/reagents present in the kits may each be in separate containers/compartments, or various components/reagents can be combined in one or more containers/compartments, depending on the sterility, cross-reactivity, and stability of the components/reagents.

In addition, the kit can further include a set of written instructions explaining how to use one or more components of the kit. A kit of this nature can be used in any of the methods described or otherwise contemplated herein.

Certain non-limiting embodiments of the present disclosure are directed to a method that includes: (1) applying any of the perforated conductive gel-containing compositions disclosed or otherwise contemplated herein to a skin of a patient; (2) applying at least one pair of transducer arrays to the perforated gel-containing composition disposed upon the patient's skin; and (3) generating an alternating electric field having a frequency in a range of from about 50 kHz to about 500 kHz for a period of time.

In certain particular (but non-limiting) embodiments, step (2) includes the application of at least two pairs of transducer arrays to the perforated conductive gel-containing composition disposed upon the patient's skin.

In certain particular (but non-limiting) embodiments, the alternating electric field is generated within a target region of the patient. The target region typically comprises at least one tumor, and the generation of the alternating electric field selectively destroys or inhibits growth of the tumor. The alternating electric field may be generated at any frequency that selectively destroys or inhibits growth of the tumor. For example (but not by way of limitation), the alternating electric field may have a frequency of about 50 kHz, about 75 kHz, about 100 kHz, about 125 kHz, about 150 kHz, about 175 kHz, about 200 kHz, about 225 kHz, about 250 kHz, about 275 kHz, about 300 kHz, about 325 kHz, about 350 kHz, about 375 kHz, about 400 kHz, about 425 kHz, about 450 kHz, about 475 kHz, or about 500 kHz, as well as a range formed from any of the above values (i.e., a range of from about 100 kHz to about 300 kHz, a range of from about 100 kHz to about 150 kHz, a range of from about 150 kHz to about 300 kHz, etc.), and a range that combines two integers that fall between two of the above-referenced values (i.e., a range of from about 32 kHz to about 333 kHz, a range of from about 78 kHz to about 298 kHz, etc.).

In certain particular (but non-limiting) embodiments, the alternating electric field may be generated at two or more different frequencies. When two or more frequencies are present, each frequency is selected from any of the above-referenced values, or a range formed from any of the above-referenced values, or a range that combines two integers that fall between two of the above-referenced values.

In certain particular (but non-limiting) embodiments, the composition and the at least one pair of transducer arrays are maintained upon the patient's skin for at least about three days.

In certain particular (but non-limiting) embodiments, the method includes the steps of: (4) removing the at least one pair of transducer arrays and the perforated conductive gel-containing composition from the patient's skin; (5) preparing the patient's skin for another treatment (such as, but not limited to, cleansing of the skin and shaving of the skin, if necessary); and (6) repeating steps (1)-(3). In addition, this cycle of steps (1)-(6) can be repeated as many times as necessary.

When steps (1)-(3) are repeated, the perforated conductive gel-containing composition and at least one pair of transducer arrays may be placed in different positions than their original placement; relocation of the arrays in this manner treatment functions to minimize any dAEs that may occur.

Referring now to the Figures, shown therein are non-limiting embodiments of various configurations of the perforated, conductive gel compositions disclosed herein. While hydrogels are specifically shown in the Figures, a person having ordinary skill in the art should readily understand that the perforated (and protrusion) configurations disclosed herein may be utilized with any conductive gel commonly known in the art.

Figure 1:
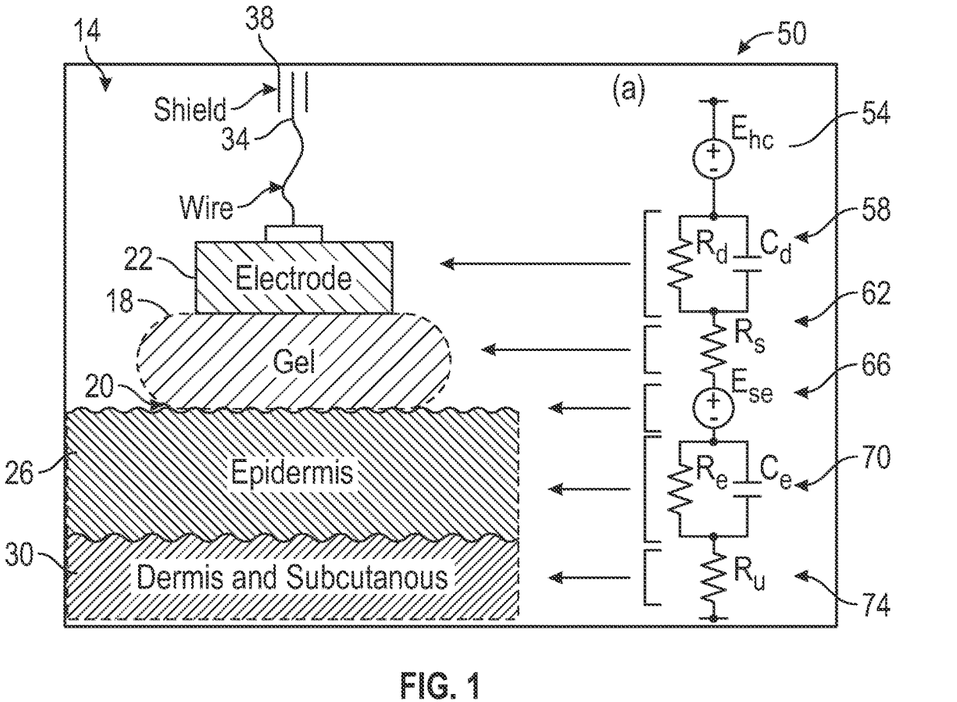
FIG. 1 is a schematic representation of an exemplary embodiment of an electrode hydrogel system constructed in accordance with the present disclosure.

Referring now to FIG. 1, shown therein is a schematic representation 10 of a TTField generating system 14 constructed in accordance with the presently disclosed and/or claimed inventive concept(s). As generally shown in FIG. 1, a hydrogel 18 provides an adhesion interface 20 for at least one insulated electrode 22 of the TTField-generating system 14 and the patient's epidermal layer 26 for delivery of at least one TTField to and/or through the patient's epidermal layer 26 and/or dermal/subcutaneous layer(s) 30. The insulated electrode 22 is electrically coupled to a wire 34, also referred to as a lead, which may include insulation 38 covering at least a portion of the wire 34.

Further shown in FIG. 1 is an electronics diagram 50 of the TTField generating system 14 constructed in accordance with the presently disclosed and/or claimed inventive concept(s). The electronics diagram 50 comprises one or more segments represented by electronic components to illustrate electrical properties of each element of the TTField generating system 14. The electronic diagram 50 generally comprises segment 54 shown as power source $E_{he}$ representing power supplied via the lead 34, the segment 54 is electrically coupled to a segment 58. The segment 58 is illustrated as a resister ($R_d$) connected in parallel with a capacitor ($C_d$). The segment 58 represents the electrode 22. The segment 58 is electrically coupled to a segment 62 comprising a resistor (Rs) and represents the hydrogel 18. The segment 62 is electrically coupled to a segment 66 comprising a power source ($E_{se}$) and represents the adhesion interface 20. The segment 66 is electrically coupled to a segment 70 comprising a resistor ($R_e$) connected in parallel with a capacitor ($C_e$) and represents the patient's epidermal layer 26. The segment 70 is electrically coupled to a segment 74 comprising a resistor ($R_u$) and represents the dermal/subcutaneous layer(s) 30.

Figure 2A:
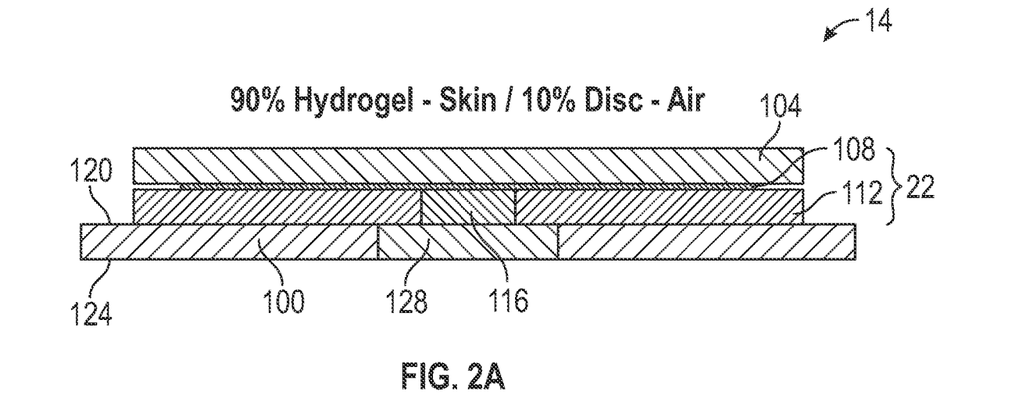
FIG. 2A is a cross-sectional view of an exemplary embodiment of a first TTField-generating system constructed in accordance with the present disclosure.

FIG. 2A shows a cross-sectional view of one non-limiting embodiment of a TTField-generating system 14 that is constructed in accordance with the presently disclosed and/or claimed inventive concept(s). As shown in FIG. 2A, the TTField system 14 comprises at least one insulated electrode 22 and a perforated hydrogel layer 100. The at least one insulated electrode 22 comprises at least one non-conducting layer 104, at least one conducting layer 108, and a high capacitance layer 112 having at least one opening 116 disposed therethrough. Also shown in FIG. 2A, the perforated hydrogel layer 100 comprises a top surface 120 and a bottom surface 124 wherein a single, central perforation 128 extends between the top surface 120 and the bottom surface 124 through the perforated hydrogel layer 100.

In one non-limiting embodiment, the at least one conducting layer 108 comprises and/or consists of at least one conducting element and/or compound, including, by way of example only, elemental silver.

In one non-limiting embodiment, the high capacitance layer 112 comprises and/or consists of ceramic and the at least one opening 116 contains and/or is coated with (for instance, the inner perimeter of the at least one opening 116 is coated) at least one epoxy.

The perforated hydrogel layer 100 may comprise any polymerizable conductive gel(s) as set forth in greater detail elsewhere herein. While shown in FIGS. 2A-2B as comprising a single central perforation 128 extending through perforated hydrogel layer 100, a person having ordinary skill in the art should readily appreciate that the perforated hydrogel layer 100 may comprise any number of perforations extending through the perforated hydrogel layer 100 capable of accomplishing the presently disclosed and/or claimed inventive concept(s), including, without limitation, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 500, 525, 550, 575, 600, 625, 650, 675, 700, 725, 750, 775, 800, 825, 850, 875, 900, 925, 950, 975, or greater than or equal to 1,000 perforations.

Figure 2B:
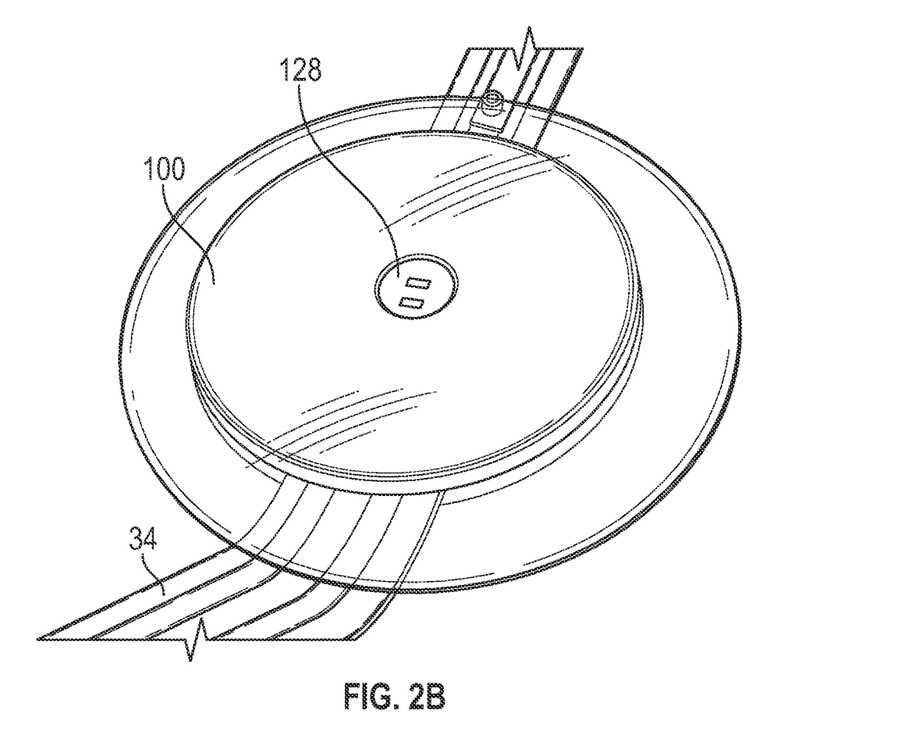
FIG. 2B is a diagram of an exemplary embodiment of a first hydrogel layer depicted in FIG. 2A.

In addition, while shown in FIGS. 2A-2B (as well as FIGS. 3A-3B discussed below in more detail) as being substantially circular in shape, a person having ordinary skill in the art should readily understand that the perforation(s), including the central perforation 128, may be any shape capable of accomplishing the presently disclosed and/or claimed inventive concept(s), including, without limitation, circular, triangular, square, rectangular, pentagonal, hexagonal (as shown in greater detail in FIG. 5), heptagonal, octagonal, nonagonal, decagonal, hendecagonal, dodecagonal, non-symmetrical shapes like a numeral 3, 4, 5, point stars, the + sign, spirals, or any shape with any number of sides capable of accomplishing the presently disclosed and/or claimed inventive concept(s). Without being bound by theory, the inventor believes that when filled with air, the perforations, including the central perforation 128, may induce an edge effect which focuses the electromagnetic fields at the air/hydrogel interface. Thus, to maximize the edge effect, perforations can be chosen which maximizes the amount of edges forming an air/hydrogel interface. For this reasons, the inventor theorize that perforations with sharp corners can also increase the edge effect. Thus, a hydrogel layer having a triangular shape perforation would have a greater number of sharp corners than a hydrogel layer having a circular perforation and would provide enhanced electromagnetic fields into the patient's body relative to the hydrogel layer having the circular perforation.

The perforation(s), including the central perforation 128, may be of any dimension capable of accomplishing the presently disclosed and/or claimed inventive concept(s), including, without limitation, a dimension in which the distance across a particular perforation is 0.1 millimeter, 0.2 millimeter, 0.3 millimeter, 0.4 millimeter, 0.5 millimeter, 0.6 millimeter, 0.7 millimeter, 0.8 millimeter, 0.9 millimeter, 1.0 millimeter, 1.1 millimeter, 1.2 millimeter, 1.3 millimeter, 1.4 millimeter, 1.5 millimeter, 1.6 millimeter, 1.7 millimeter, 1.8 millimeter, 1.9 millimeter, 2.0 millimeters, 2.1 millimeters, 2.2 millimeters, 2.3 millimeters, 2.4 millimeters, 2.5 millimeters, 2.6 millimeters, 2.7 millimeters, 2.8 millimeters, 2.9 millimeters, 3.0 millimeters, 3.1 millimeters, 3.2 millimeters, 3.3 millimeters, 3.4 millimeters, or greater than or equal to 3.5 millimeters. When the perforated hydrogel layer 100 comprises more than one perforation, the perforations may have the same or different dimension(s).

The perforation(s), including the central perforation 128, may be formed in and through the perforated hydrogel layer 100 via any technique capable of accomplishing the presently disclosed and/or claimed inventive concept(s), including, without limitation, via dye-cutting techniques and/or laser-cutting techniques. The formation of the perforations in and through the perforated hydrogel layer may be accomplished via an automated or non-automated process(es).

In the non-limiting embodiment shown in FIGS. 2A-2B, about 90% of the perforated hydrogel layer 100 adheres to the patient's epidermal layer 26, while the single, central perforation 128 comprises about 10% of the perforated hydrogel layer 100. As can be seen below in Table 1A, a first test shows that the above-described perforated hydrogel layer 100 comprising the single, central perforation 128 introduces air under the high capacitance layer 112 via the single, central perforation 128 which results in a 60% increase in conductivity as compared to an exemplary non-perforated hydrogel, as well as a reduction in operating temperature from 40° C. to 37.2° C. In addition, as shown below in Table 1B, a second test shows that the above-described perforated hydrogel layer 100 comprising the single, central perforation 128 introduces air under the high capacitance layer 112 via the single, central perforation 128 which results in a 105% increase conductivity as compared to an exemplary non-perforated hydrogel, as well as a reduction in operating temperature from 39.6° C. to 38.1° C.

TABLE 1A

Comparison of Non-Perforated Hydrogel and Perforated Hydrogel layer 100 Shown in FIGS. 2A-2B (Test 1)

| Parameter | Non-Perforated Hydrogel | Perforated Hydrogel layer 100 Shown in FIGS. 2A-2B |
| --- | --- | --- |
| Conductance (Current) | 1950 mA | 3136 mA |
| Voltage | 75 V | 100 V |
| Resistance | 38 ohms | 31 ohms |
| Operating Temperature (Max) | 40° C. | 37.2° C. |
| % Increase in Conductance | (1950 mA − 3136 mA)/1950 mA = ~60.82% Increase | |

TABLE 1B

Comparison of Non-Perforated Hydrogel and Perforated Hydrogel layer 100 Shown in FIGS. 2A-2B (Test 2)

| Parameter | Non-Perforated Hydrogel | Perforated Hydrogel layer 100 Shown in FIGS. 2A-2B |
| --- | --- | --- |
| Conductance (Current) | 1554 mA | 3197 mA |
| Voltage | 59 V | 101 V |
| Resistance | 37 ohms | 31 ohms |
| Operating Temperature (Max) | 39.6° C. | 38.1° C. |
| % Increase in Conductance | (1554 mA − 3197 mA)/1554 mA = ~105.73% Increase | |

Figure 3A:
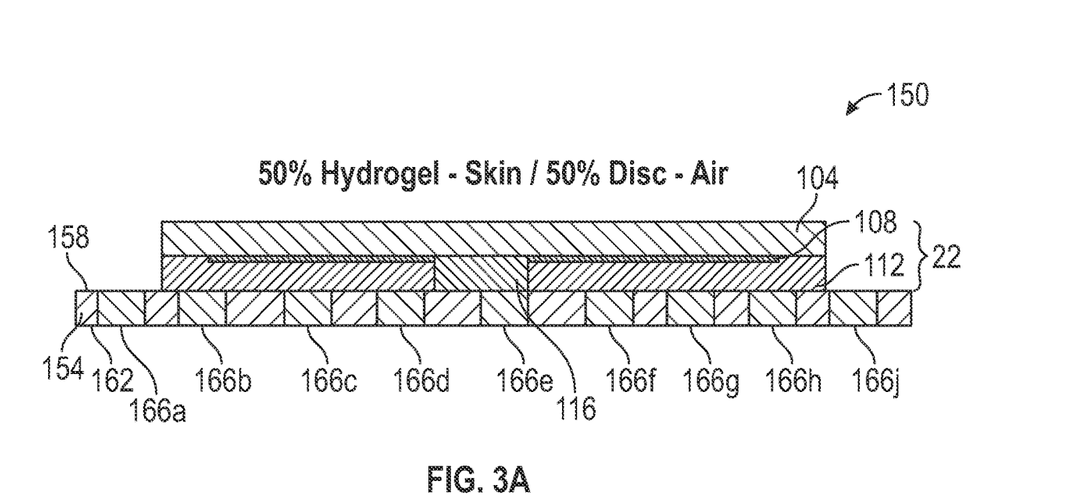
FIG. 3A is a cross-sectional view of an exemplary embodiment of a second TTField-generating system constructed in accordance with the present disclosure.

Referring now to FIG. 3A, shown therein is a cross-sectional view of one non-limiting embodiment of a TTField-generating system 150 that is constructed in accordance with the presently disclosed and/or claimed inventive concept(s). The insulated electrode 22 comprising the at least one non-conducting layer 104, at least one conducting layer 108, and the high capacitance layer 112 having at least one opening 116 disposed therethrough of the TTField-generating system 150 are identical in both construction and description to those elements of the TTField-generating system 14 as described with reference to FIGS. 2A-2B. Accordingly, no additional description is deemed necessary.

The TTField-generating system 150 comprises a second perforated hydrogel layer 154 that comprises a top surface 158 and a bottom surface 162 wherein multiple perforations 166a-j extend from the top surface 158 to the bottom surface 162 through the second perforated hydrogel layer 154. In the non-limiting embodiment shown in FIGS. 3A-3B, about 50% of the second perforated hydrogel layer 154 adheres to the patient's epidermal layer 26 while about 50% of the second perforated hydrogel layer 154 includes the multiple perforations 166a-j. As can be seen below in Table 2, increased introduction of air under the high capacitance layer 112 via the multiple perforations 166a-j within the second perforated hydrogel layer 154 results in a 14% increase in conductance, as compared to an exemplary non-perforated hydrogel, as well as a reduction in operating temperature from 36.6° C. to 34° C.

TABLE 2

Figure 3B:
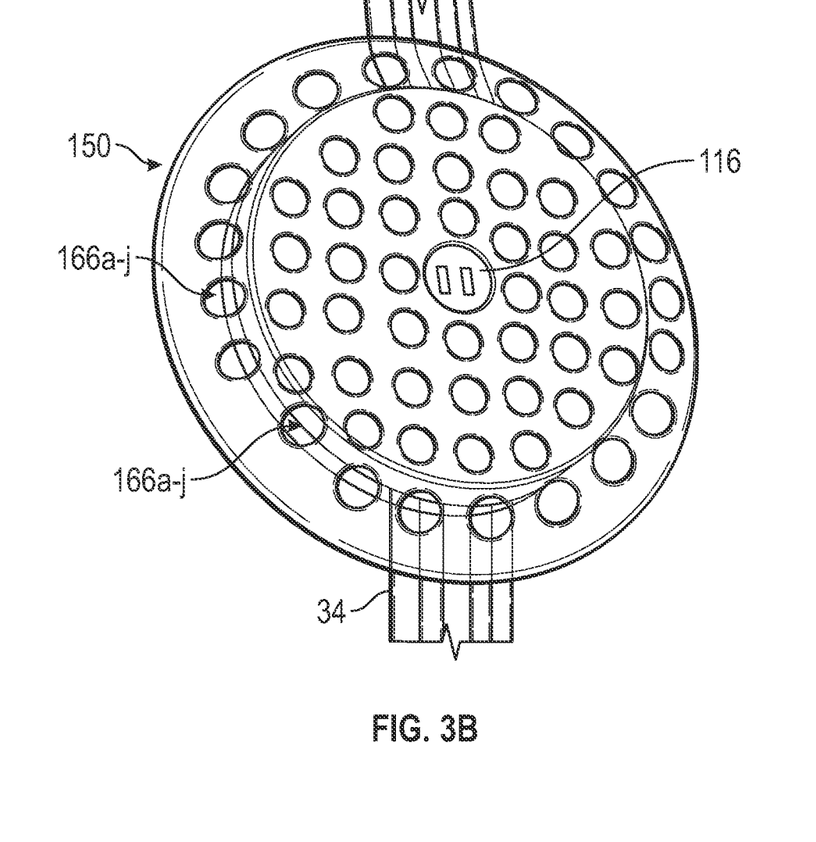
FIG. 3B is a diagram of a second hydrogel layer depicted in FIG. 3A.

Comparison of Non-Perforated Hydrogel and Second Perforated Hydrogel Layer 154 as Shown in FIGS. 3A-3B

| Parameter | Non-Perforated Hydrogel | Second Perforated Hydrogel layer 154 Shown in FIGS. 3A-3B |
| --- | --- | --- |
| Conductance (Current) | 2312 mA | 2642 mA |
| Voltage | 107 V | 93 V |
| Resistance | 46 ohms | 35 ohms |
| Operating Temperature (Max) | 36.6° C. | 34.0° C. |
| % Increase in Conductance | (2312 mA − 2642 mA)/2312 mA = ~14.27% Increase | |

Figure 4A:
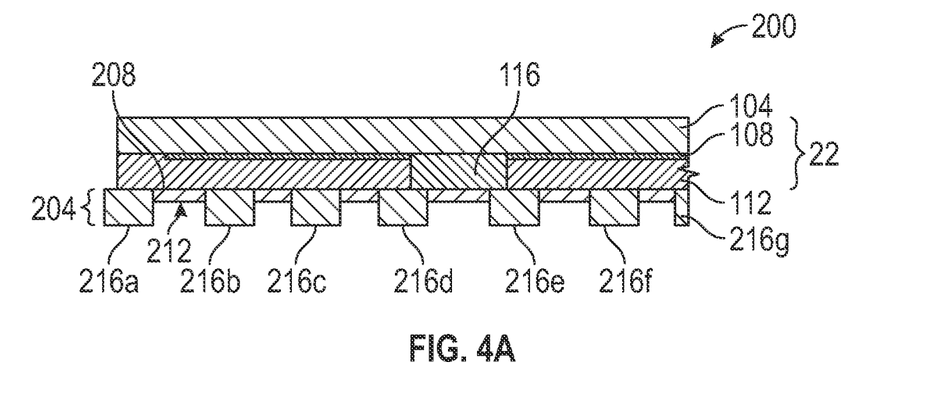
FIG. 4A is a cross-sectional view of an exemplary embodiment of a third TTField-generating system constructed in accordance with the present disclosure.

Referring now to FIG. 4A, shown therein is a cross-sectional view of one non-limiting embodiment of a TTField-generating system 200 that is constructed in accordance with the presently disclosed and/or claimed inventive concept(s). The at least one electrode 22 comprising the at least one non-conducting layer 104, at least one conducting layer 108, and the high capacitance layer 112 having at least one opening 116 disposed therethrough of the TTField-generating system 200 are identical in both construction and description to those elements of the TTField generating system 14 as described with reference to FIGS. 2A-2B. Accordingly, no additional description is deemed necessary.

In this non-limiting embodiment, the hydrogel layer 204 comprises a top surface 208 that substantially adheres to the high capacitance layer 112, a bottom surface 212, and at least one protrusion 216a-g extending from the bottom surface 212 of the hydrogel layer 204. The at least one protrusion 216a-g engage and adhere to the patient's epidermal layer 26, while pockets of air are introduced as a result of spacing between the at least one protrusion 216a-g.

The number of protrusions 216a-g present on the bottom surface 212 of the hydrogel layer 204 may be any number of protrusions 216a-g capable of accomplishing the presently disclosed and/or claimed inventive concept(s), including, without limitation, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 500, 525, 550, 575, 600, 625, 650, 675, 700, 725, 750, 775, 800, 825, 850, 875, 900, 925, 950, 975, or greater than or equal to 1,000 protrusions. Each protrusion 216a-g may be any shape capable of accomplishing the presently disclosed and/or claimed inventive concept(s). In addition, each protrusion 216a-g may be the same shape, different shapes, and/or have the same or different dimensions as one or more other protrusion 216a-g. In one non-limiting embodiment, each protrusion 216a-g may be of any height (i.e., the distance from the bottom surface 212 to the patient's epidermal layer 26) capable of accomplishing the presently disclosed and/or claimed inventive concept(s), including, without limitation, a height of about 0.1 millimeter, about 0.2 millimeter, about 0.3 millimeter, about 0.4 millimeter, about 0.5 millimeter, about 0.6 millimeter, about 0.7 millimeter, about 0.8 millimeter, about 0.9 millimeter, about 1.0 millimeter, about 1.1 millimeter, about 1.2 millimeter, about 1.3 millimeter, about 1.4 millimeter, about 1.5 millimeter, about 1.6 millimeter, about 1.7 millimeter, about 1.8 millimeter, about 1.9 millimeter, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, about 3.0 millimeters, about 3.1 millimeters, about 3.2 millimeters, about 3.3 millimeters, about 3.4 millimeters, or greater than or equal to about 3.5 millimeters.

In one non-limiting embodiment, each protrusion 216a-g may be any diameter capable of accomplishing the presently disclosed and/or claimed inventive concept(s), including, without limitation, a diameter of about 0.1 millimeter, about 0.2 millimeter, about 0.3 millimeter, about 0.4 millimeter, about 0.5 millimeter, about 0.6 millimeter, about 0.7 millimeter, about 0.8 millimeter, about 0.9 millimeter, about 1.0 millimeter, about 1.1 millimeter, about 1.2 millimeter, about 1.3 millimeter, about 1.4 millimeter, about 1.5 millimeter, about 1.6 millimeter, about 1.7 millimeter, about 1.8 millimeter, about 1.9 millimeter, about 2.0 millimeters, about 2.1 millimeters, about 2.2 millimeters, about 2.3 millimeters, about 2.4 millimeters, about 2.5 millimeters, about 2.6 millimeters, about 2.7 millimeters, about 2.8 millimeters, about 2.9 millimeters, about 3.0 millimeters, about 3.1 millimeters, about 3.2 millimeters, about 3.3 millimeters, about 3.4 millimeters, or greater than or equal to about 3.5 millimeters. When the hydrogel layer 204 comprises more than one protrusion 216, the more than one protrusion 216a-g may have the same or different dimension(s). In one non-limiting embodiment, each or all of the one or more protrusion 216a-g may be tapered, wherein a portion of a particular protrusion 216 formed on the bottom surface 212 may have a larger diameter than a portion of that particular protrusion 216 contacting the patient's epidermal layer 26. Similarly, a portion of a particular protrusion 216 formed on the bottom surface 212 may have a smaller diameter than a portion of that particular protrusion 216 contacting the patient's epidermal layer 26.

Figure 4B:
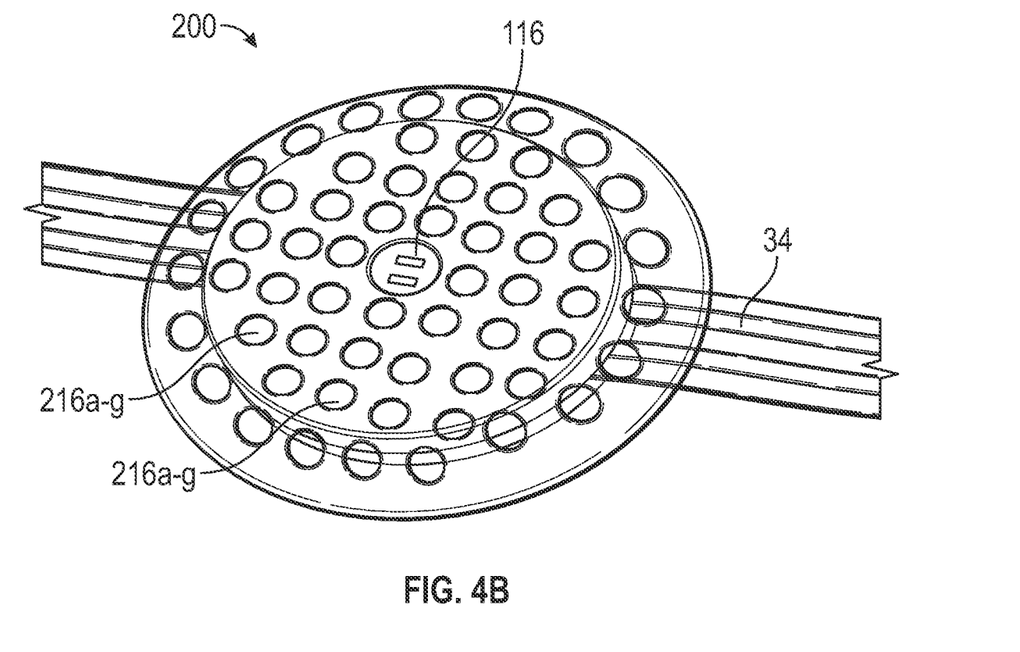
FIG. 4B is a diagram of a third hydrogel layer depicted in FIG. 4A.

In the non-limiting embodiment shown in FIGS. 4A-4B, about 50% of the hydrogel layer 204 adheres to the patient's epidermal layer 26 while the at least one protrusion 216a-g comprise about 50% of the hydrogel layer 204.

Figure 5:
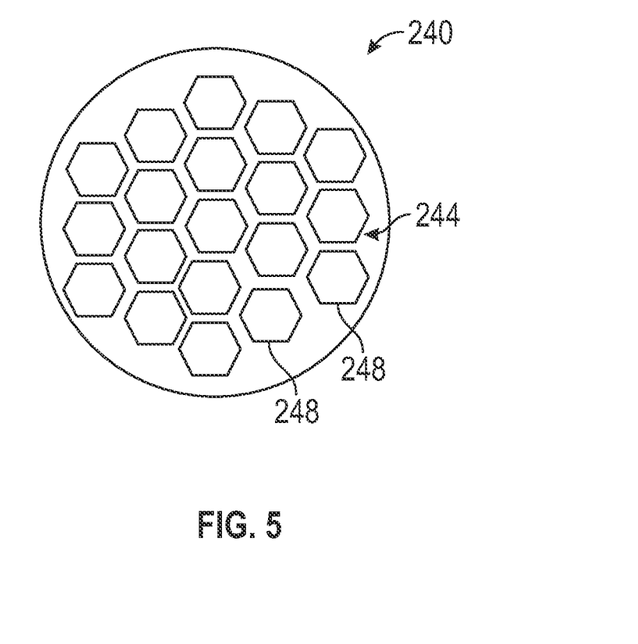
FIG. 5 is a diagram of an exemplary embodiment of a fourth hydrogel layer constructed in accordance with the present disclosure.

Referring now to FIG. 5, shown therein is a diagram of an exemplary embodiment of a third perforated hydrogel layer 240 comprising a hydrogel portion 244 and a plurality of perforations 248. Only two of the perforations 248 are labeled in FIG. 5 for purposes of brevity. The third perforated hydrogel layer 240 is generally constructed in accordance with the second perforated hydrogel layer 154, described in more detail above, with the exception that the plurality of perforations 248 have a hexagonal shape.

Figure 6A:
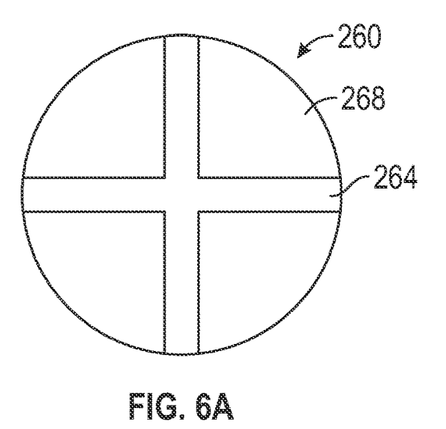
FIG. 6A is a diagram of an exemplary embodiment of a fifth hydrogel layer constructed in accordance with the present disclosure.
Figure 6B:
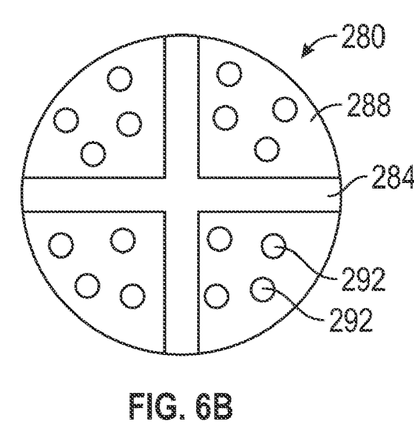
FIG. 6B is a diagram of an exemplary embodiment of a sixth hydrogel layer constructed in accordance with the present disclosure.
Figure 6C:
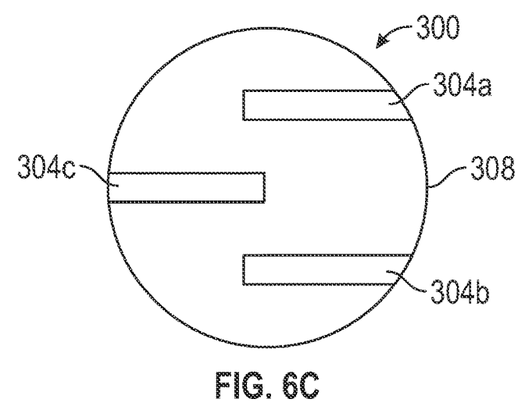
FIG. 6C is a diagram of an exemplary embodiment of a seventh hydrogel layer constructed in accordance with the present disclosure.

Referring now to FIGS. 6A-6C, shown therein are non-limiting embodiments and configurations of a perforated hydrogel layer constructed in accordance with the present disclosure. Shown in FIG. 6A is a hydrogel layer 260 comprising one or more channel 264 formed within hydrogel 268. Shown in FIG. 6B is a hydrogel layer 280 comprising one or more channel 284 formed within hydrogel 288 and a plurality of perforations 292 constructed in accordance with the perforations 166a-j described in more detail above. Shown in FIG. 6C is a hydrogel layer 300 comprising one or more channel 304a-c formed within hydrogel 308. As can be seen in these figures, the perforated hydrogel layer may comprise a plurality of air channel 264, 684, 304a-c (FIGS. 6A and 6C) and/or a combination of a plurality of channels 284 and perforations 292 (FIG. 6B). Each of the channel 264, 284, 304a-c and perforation 292 allows for the introduction and flow of air underneath the respective hydrogel layer 260, 280, 300 thereby allowing for the benefits of the presently disclosed and/or claimed inventive concept(s) as described elsewhere herein. A hydrogel layer is not limited to the configurations of air channels and/or perforations shown in FIGS. 6A-C. In other embodiments, a hydrogel layer may have other configurations or combinations of air channels and/or perforations such as non-linear air channels and/or one or more perforations extending through an air channel.

Figure 7:
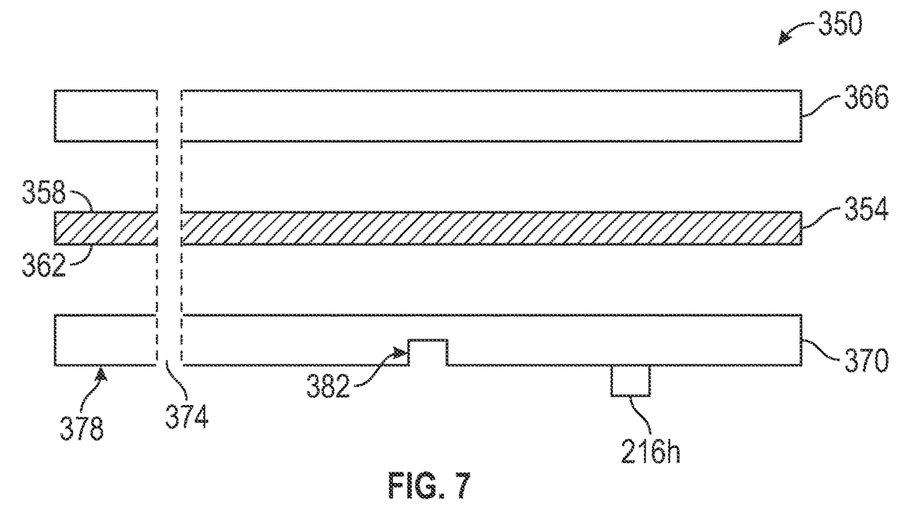
FIG. 7 is an exploded diagram of an exemplary embodiment of a conductive gel constructed in accordance with the present disclosure.

Referring now to FIG. 7, shown therein is an exploded diagram of an exemplary embodiment of conductive gel 350. As shown, the conductive gel 350 is a multi-layer structure that comprises at least a scrim layer 354 having a first side 358 and a second side 362, a gel tie layer 366 attached to the first side 358 of the scrim layer 354, and a gel skin layer 370 attached to the second side 362 of the scrim layer 354. The gel tie layer 366 is designed for contact with the at least one insulated electrode 22 of the TTField-generating system 14, while the gel skin layer 370 is designed for contact with the patient's skin, e.g., the epidermis layer 26. The gel tie layer 366 and gel skin layer 370 are each formed of any of the conductive gels described or otherwise contemplated herein, and may be formed of the same or different conductive gel.

In one embodiment, the scrim layer 354 may be formed of any material that allows the composition to function in accordance with the present disclosure; in particular, the material from which the scrim layer 354 is formed is typically selected to optimize conductivity and minimize resistance of the composition. A non-limiting example of a material from which the scrim layer 354 can be formed is spun nylon. In certain non-limiting embodiments, the conductive gel 350 comprises and/or consists of at least one perforation (e.g., perforation 374) extending through the entirety of the multi-layer structure of the conductive gel 530, that is, each perforation 374 may extend through at least the gel tie layer 366, the scrim layer 354, and the gel skin layer 370. In certain non-limiting embodiments, the conductive gel 350 comprises at least one protrusion 216 (e.g., protrusion 216h) extending from a first side 378 of the gel skin layer 370 that engaged a patient's skin 26. In one embodiment, the gel skin layer 370 of the conductive gel 350 may be formed in accordance with the hydrogel layer 260, 280, and/or 300 shown in FIGS. 6A-C and described in more detail above, such that the gel skin layer 370 comprises one or more channel 382 formed within the gel skin layer 370 and in accordance with the one or more channel 264, 284, and/or 304a-c.

In one embodiment, the conductive gel 350 comprises one or more of: at least one perforation 374, extending through at least the gel tie layer 366, the scrim layer 354, and the gel skin layer 370; at least one protrusion 216 extending from the first side 378 of the gel skin layer 370; and at least one channel 382 operable to allow for introduction and flow of air between the first side 378 of the gel skin layer 370 and the patient's epidermal layer 26.

Alternative constructions for the transducer arrays may also be used, including, for example, transducer arrays that use dielectric ceramic elements that are not disc-shaped, and transducer arrays that use non-ceramic dielectric materials positioned over a plurality of flat conductors. Examples of the latter include polymer films disposed over conductive pad(s) on a printed circuit board or over one or more flat pieces of a conductive material, such as a metallic material. Exemplary metallic materials include copper, gold, silver, and aluminum. Transducer arrays that use electrode elements that are not capacitively coupled into the patient's body may also be used. In this situation, each element of the transducer array would be implemented using a region of a conductive material that is configured for placement against a person's body, or against a conductive gel that is placed against the person's body with no insulating dielectric layer disposed between the conductive material or the conductive gel and the body. Other alternative constructions for implementing the transducer arrays may also be used, as long as they are (a) capable of delivering TTFields to the person's body and (b) positioned in the locations specified herein. Optionally, a layer of conductive gel, such as a hydrogel, may be disposed between the transducer arrays and the person's body in any of the embodiments described herein.

Non-Limiting Illustrative Embodiments of the Inventive Concept(s)

Illustrative embodiment 1. A hydrogel, comprising: a polymerized conductive hydrogel for application to a patient's skin and for placement between the patient's skin and at least one transducer array that generates an alternating electric field having a frequency in a range of from about 50 kHz to about 500 kHz, wherein the polymerized conductive hydrogel comprises a top surface and a bottom surface, further wherein the polymerized conductive hydrogel comprises at least one perforation extending from the top surface to the bottom surface through the polymerized conductive hydrogel.

Illustrative embodiment 2. The hydrogel of illustrative embodiment 1, wherein at least one perforation is circular in shape.

Illustrative embodiment 3. The hydrogel of illustrative embodiment 2, wherein the at least one perforation has a diameter of about 3.175 millimeters.

Illustrative embodiment 4. The hydrogel of illustrative embodiment 1, wherein the at least one perforation is hexagonal in shape.

Illustrative embodiment 5. A hydrogel, comprising: a polymerized conductive hydrogel for application to a patient's skin and for placement between the patient's skin and at least one transducer array that generates an alternating electric field having a frequency in a range of from about 50 kHz to about 500 kHz, wherein the polymerized conductive hydrogel comprises a top surface and a bottom surface, further wherein the polymerized conductive hydrogel comprises at least one protrusion extending from the bottom surface of the polymerized conductive hydrogel.

Illustrative embodiment 6. The hydrogel of any one of illustrative embodiments 1-5, wherein the hydrogel is sterile.

Illustrative embodiment 7. The hydrogel of any one of illustrative embodiments 1-6, wherein the hydrogel a polyacrylic acid gel, a povidone gel, or a cellulose gel.

Illustrative embodiment 8. The hydrogel of any one of illustrative embodiments 1-6, wherein the hydrogel comprises at least one of chitosan, alginate, agarose, methylcellulose, hyaluronan, collagen, laminin, matrigel, fibronectin, vitronectin, poly-1-lysine, proteoglycans, fibrin glue, gels made by decellularization of engineered and natural tissues, and a combination thereof.

Illustrative embodiment 9. The hydrogel of illustrative embodiment 8, wherein the gel comprises at least one of polyglycolic acid (PGA), polylactic acid (PLA), poly-caprolactone (PCL), polyvinyl alcohol (PVA), polyethylene glycol (PEG), methyl methacrylate, poly(methyl methacrylate) (PMMA), poly(2-hydroxyethyl methacrylate) (Poly-HEMA), poly(glycerol sebacate), polyurethanes, poly(isopropylacrylamide), poly(N-isopropylacrylamide), or any combination thereof.

Illustrative embodiment 10. The hydrogel of any one of illustrative embodiments 1-9, wherein the hydrogel has a pH in a range of from about 6.5 to about 7.5

Illustrative embodiment 11. The hydrogel of any one of illustrative embodiments 1-10, wherein the skin adhesion of the hydrogel is at least about 120 g/inch.

Illustrative embodiment 12. The hydrogel of any one of illustrative embodiments 1-11, wherein the hydrogel has a thickness in a range of from about 10 mil to about 50 mil.

Illustrative embodiment 13. The hydrogel of any one of illustrative embodiments 1-12, wherein the hydrogel has a shelf life of at least about six months.

Illustrative embodiment 14. A TTField-generating system, comprising: at least one insulated electrode, the at least one electrode comprising at least one non-conducting layer, at least one conducting layer, and a high capacitance layer having a top surface and a bottom surface, wherein at least one opening is disposed between the top surface and the bottom surface of the high capacitance layer, further wherein the at least one electrode generates an alternating electric field having a frequency in a range from about 50 kHz to about 500 kHz; and at least one perforated hydrogel, the at least one perforated hydrogel comprising a polymerized conductive gel having a top surface and a bottom surface, wherein the top surface of the perforated hydrogel adheres to the bottom surface of the high capacitance layer and the bottom surface of the perforated hydrogel adheres to a patient's skin, further wherein the perforated hydrogel comprises at least one perforation extending from the top surface to the bottom surface through the perforated hydrogel.

Illustrative embodiment 15. The TTField-generating system of illustrative embodiment 14, wherein the TTField-generating system is integrated into a transducer array.

Illustrative embodiment 16. The transducer array of illustrative embodiment 15, wherein the transducer array comprises at least two TTField-generating systems.

Illustrative embodiment 17. The TTField-generating system of any one of illustrative embodiments 14-16, wherein the perforated hydrogel has a pH in a range of from about 6.5 to about 7.5.

Illustrative embodiment 18. The TTField-generating system of any one of illustrative embodiments 14-17, wherein the at least one perforated hydrogel is sterile.

Illustrative embodiment 19. The TTField-generating system of any one of illustrative embodiments 14-18, wherein the at least one perforation is circular in shape.

Illustrative embodiment 20. The TTField-generating system of any one of illustrative embodiments 14-18, wherein the at least one perforation is hexagonal in shape.

Illustrative embodiment 21. The TTField-generating system of any one of illustrative embodiments 14-20, wherein the skin adhesion rate of the perforated hydrogel is at least about 120 g/inch.

While the attached disclosures describe the inventive concept(s) in conjunction with the specific experimentation, results, and language set forth hereinafter, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A tumor treating field system, comprising:
   a transducer array operable to receive a power from a power source and generate an alternating electric field having a frequency in a range of from about 50 kHz to about 500 kHz when paired with a second transducer array, the transducer array comprising at least a conducting layer having a first surface and a second surface, and a high capacitance layer having a first surface in contact with the second surface of the conducting layer, a second surface, and a first perforation wall extending from the second surface of the high capacitance layer to the first surface of the high capacitance layer thereby forming a first perforation; and a hydrogel layer, the hydrogel layer comprising a polymerized conductive hydrogel for application to a patient's skin and for placement between the patient's skin and the transducer array, wherein the hydrogel layer comprises a top surface in contact with the second surface of the high capacitance layer and a bottom surface, further wherein the hydrogel layer comprises a second perforation wall extending from the top surface of the hydrogel layer to the bottom surface of the hydrogel layer through the polymerized conductive hydrogel; the second perforation wall forming a second perforation aligned with the first perforation.

2. The tumor treating field system of claim 1, wherein the perforation is circular in shape.

3. The tumor treating field system of claim 2, wherein the perforation has a diameter of about 3.175 millimeters.

4. The tumor treating field system of claim 1, wherein the perforation is hexagonal in shape.

5. The tumor treating field system of claim 1, wherein the first perforation has a having a first cross-sectional dimension extending across the first perforation, and the second perforation has a second cross-sectional dimension extending across the second perforation, and wherein the second cross-sectional dimension is larger than the first cross-sectional dimension.

6. A tumor treating field system, comprising:
a transducer array operable to receive a power from a power source and generate an alternating electric field having a frequency in a range of from about 50 kHz to about 500 kHz when paired with a second transducer array, the transducer array comprising at least a conducting layer having a first surface and a second surface, and a high capacitance layer having a first surface in contact with the second surface of the conducting layer and a second surface; and a hydrogel layer, the hydrogel layer comprising a polymerized conductive hydrogel for application to a patient's skin and for placement between the patient's skin and the transducer array, wherein the hydrogel layer comprises a top surface in contact with the second surface of the high capacitance layer and a bottom surface operable to contact the patient's skin, further wherein the hydrogel layer comprises at least one protrusion extending from the bottom surface of the hydrogel layer.

7. The tumor treating field system of claim 6, wherein the hydrogel layer is sterile.

8. The tumor treating field system of claim 6, wherein the hydrogel layer is a polyacrylic acid gel, a povidone gel, or a cellulose gel.

9. The tumor treating field system of claim 6, wherein the polymerized conductive hydrogel comprises at least one of chitosan, alginate, agarose, methylcellulose, hyaluronan, collagen, laminin, matrigel, fibronectin, vitronectin, poly-1-lysine, proteoglycans, fibrin glue, gels made by decellularization of engineered and natural tissues, and a combination thereof.

10. The tumor treating field system of claim 9, wherein the polymerized conductive hydrogel comprises at least one of polyglycolic acid (PGA), polylactic acid (PLA), polycaprolactone (PCL), polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), polyurethanes, poly(isopropylacrylamide), poly(N-isopropylacrylamide), or any combination thereof.

11. The tumor treating field system of claim 6, wherein the polymerized conductive hydrogel has a pH in a range of from about 6.5 to about 7.5.

12. The tumor treating field system of claim 6, wherein the polymerized conductive hydrogel has a skin adhesion of at least about 120 g/inch.

13. The tumor treating field system of claim 6, wherein the polymerized conductive hydrogel has a thickness in a range of from about 10 mil to about 50 mil.

14. The tumor treating field system of claim 6, wherein the polymerized conductive hydrogel has a shelf life of at least about six months.

15. A TTField-generating system, comprising:
at least one insulated electrode, the at least one electrode comprising at least one non-conducting layer, at least one conducting layer, and a high capacitance layer having a top surface and a bottom surface, wherein at least one opening is disposed between the top surface and the bottom surface of the high capacitance layer, further wherein the at least one conducting layer is operable to receive power from a power source and is configured to generate an alternating electric field having a frequency in a range from about 50 kHz to about 500 kHz upon receiving the power; and at least one perforated hydrogel, the at least one perforated hydrogel comprising a polymerized conductive gel having a top surface and a bottom surface, wherein the top surface of the perforated hydrogel adheres to the bottom surface of the high capacitance layer and the bottom surface of the perforated hydrogel configured to adhere to a patient's skin, further wherein the perforated hydrogel comprises at least one perforation extending from the top surface to the bottom surface through the perforated hydrogel.

16. The TTField-generating system of claim 15, wherein the TTField-generating system is integrated into a transducer array.

17. The TTField-generating system of claim 15, wherein the perforated hydrogel has a pH in a range of from about 6.5 to about 7.5.

18. The TTField-generating system of claim 15, wherein the at least one perforated hydrogel is sterile.

19. The TTField-generating system of claim 15, wherein the at least one perforation is circular in shape.

20. The TTField-generating system of claim 15, wherein the at least one perforation is hexagonal in shape.

21. The TTField-generating system of claim 15, wherein the skin adhesion rate of the perforated hydrogel is at least about 120 g/inch.

* * * * *